United States Patent [19]

Welstead, Jr.

[11] 3,984,557
[45] Oct. 5, 1976

[54] ANTIARRHYTHMIA COMPOSITIONS AND METHODS

[75] Inventor: William John Welstead, Jr., Richmond, Va.

[73] Assignee: A. H. Robins Company, Incorporated, Richmond, Va.

[22] Filed: Dec. 26, 1974

[21] Appl. No.: 536,521

[52] U.S. Cl. .............................................. 424/263
[51] Int. Cl.² ........................................ A61K 31/44
[58] Field of Search ............... 424/263; 260/293.71, 260/294.9

[56] References Cited
UNITED STATES PATENTS

| | | | |
|---|---|---|---|
| 3,192,210 | 6/1965 | Lunsford et al. | 260/247.2 |
| 3,509,171 | 4/1970 | Welstead et al. | 260/326.3 |
| 3,687,956 | 8/1972 | Ziukovic | 260/293.83 |
| 3,806,526 | 4/1974 | Carr et al. | 260/293.64 |

Primary Examiner—Leonard Schenkman

[57] ABSTRACT

1-R-3-Pyrrolidinyl-α-phenyl-α-(2-pyridyl)acetamides, -acetonitriles and -methanes represented by the following formula:

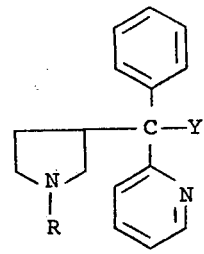

wherein R represents lower alkyl, lower cycloalkyl or phenyllower alkyl and Y is carbamoyl, cyano or hydrogen having antiarrhythmic activity are disclosed. Pharmaceutically acceptable acid addition salts are included as part of the invention.

14 Claims, No Drawings

ANTIARRHYTHMIA COMPOSITIONS AND METHODS

FIELD OF INVENTION

The present invention relates to certain heterocyclic organic compounds which may be referred to as $\alpha,\alpha,\alpha$-trisubstituted acetamides-, acetonitriles and -methanes and is more particularly concerned with 1-R-3-pyrrolidinyl-$\alpha$-phenyl-$\alpha$-(2-pyridyl)-acetamides, -acetonitriles and -methanes, compositions containing the same as active ingredients and methods of using them.

Certain compounds in the present application especially the 1-R-3-pyrrolidinyl-$\alpha$-phenyl-$\alpha$-(2-pyridyl)acetamides (and -acetonitriles) are disclosed as intermediates in U.S. Pat. Nos. 3,192,206, 3,192,210, 3,192,221 and 3,192,230.

SUMMARY OF INVENTION

The present invention is especially concerned with heterocyclic organic compounds, compositions containing said compounds as active ingredients and methods of using said compositions in controlling cardiac arrhythmias, said compounds having the formula:

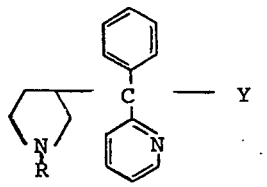

Formula I wherein;
R is lower alkyl, lower cycloalkyl, or phenyllower alkyl;
Y is carbamoyl, cyano or hydrogen, and
the pharamceutically acceptable acid addition salts thereof.

The compounds having the foregoing Formula I have at least two asymmetric centers. At least one pair of diastereoisomers therefore exists for each compound. Use of the diastereoisomers, or their optically active forms, is included within the scope of the present invention. The optically active forms of the diastereoisomers may be obtained by combining the basic racemic form with an optically active organic acid and separating by fractional crystallization the d- and l-forms. The connotation of the general Formula I presented herein therefore is to include all isomers, the separated d and l isomers as well as all mixtures of these isomers.

DETAILED DESCRIPTION OF INVENTION

The compounds described hereinafter and represented by the foregoing Formula I have been shown by accepted pharmacological procedures to have utility as physiologically active agents and particularly as effective antiarrhythmic agents, therapeutically applicable in the treatment of cardiac arrhythmias.

The action of certain compounds disclosed in the present invention in counteracting cardiac arrhythmia is demonstrated by the following procedure. The procedure is carried out under barbiturate anesthesia using adult mongrel drops of either sex weighing from 8 to 14 kg. A Grass Model 7 polygraph was used for recording femoral arterial blood pressure (Statham P23AC transducer) and the electrocardiagram (Grass 7P4 preamplifier). Ouabain was given intravenously in an initial dose of 40$\gamma$ per kg, in a second dose of 20$\gamma$/kg given 30 minutes after the first dose, and in subsequent doses of 10$\gamma$ per kg which were repeated at 15 minute intervals as required for producing cardiac arrhythmias that persisted for at least 15 minutes. When the arrhythmias were established, the test compounds were administered by infusion (Harvard Model 942 infusion pump) into a femoral vein at a rate of 1 mg/kg/minute. Concentrations of compounds were adjusted according to the weight of the dog to allow a volume infusion of 1 ml. per minute. Compounds that are considered to be active as antiarrhythmic agents cause reversion to sinus rhythm which is maintained for at least 60 minutes. The results are summarized in the following Table 1.

TABLE 1

| Antiarrhythmic Activity: Termination of Ouabain-induced Arrhythmia in Anesthetized Dogs | | |
|---|---|---|
| Compound | No Times Active/ No. Expts. | Effective Dose (mean) mg/kg |
| Example 2 | 1/2 | 8.0* |
| Example 3 | 2/2 | 1.8 |
| Example 4 | 2/2 | 8.0 |
| Example 6 | 2/2 | 3.0 |
| Example 8 | 5/5 | 1.9 |
| Example 9 | 1/2 | 1.5* |
| Example 10 | 2/2 | 3.8 |
| Example 13 | 2/3 | 8.5 |

*Result of single experiment in which compound was active

It is, accordingly, an object of the present invention to provide compounds with a high degree of antiarrhythmic activity. An additional object is the provision of compounds having antiarrhythmic activity and which produce minimal side effects. A further object is to provide pharmaceutical compositions containing antiarrhythmic effective amounts of the compounds as active ingredients. A still further object is to provide a method of using said antiarrhythmic agents in the treatment of living animal and especially mammalian bodies. Additional objects will be apparent to one skilled in the art and still other objects will become apparent hereinafter.

The invention also includes pharmaceutically acceptable acid addition salts of the above bases and the optical isomers thereof which are formed with nontoxic organic and inorganic acids. Such salts are usually prepared by methods known to the art. The base is reacted with either the calculated amount of organic or inorganic acid in aqueous miscible solvent, such as ethanol or isopropanol, with isolation of the salt by concentration and cooling or with an excess of the acid in an aqueous immiscible solvent, such as ethyl ether or isopropyl ether, with the desired salt separating directly. Exemplary of such organic salts are those with maleic, fumaric, benzoic, ascorbic, tartaric, malic, and citric acid and the like. Exemplary of such inorganic salts are those with hydrochloric, hydrobromic, sulfuric, phosphoric and nitric acids.

In the definitions of symbols in the foregoing Formula I and where they appear elsewhere throughout this specification, the terms have the following significance.

The term "loweralkyl" as used herein includes straight and branched chain radicals of from 1 to 8 carbon atoms inclusive. Examples of loweralkyl radicals are methyl, ethyl, propyl, n-butyl, isopropyl, isobutyl, amyl, isoamyl, hexyl, heptyl, octyl, isooctyl, and the like.

The term "lower cycloalkyl" as used herein includes primarily cyclic radicals containing 3 to 9 carbon atoms inclusive and encompasses such groups as cyclopropyl, cyclobutyl, cyclopentyl, cyclohexyl, methylcyclohexyl, propylcyclohexyl, cycloheptyl, and cyclooctyl.

The term "phenyl loweralkyl" as used herein includes loweralkyl, substituted phenyl groups such as benzyl, phenethyl, methylbenzyl, phenpropyl, and the like.

The starting material for the compounds of the present invention is α-phenyl-α-(2-pyridyl)acetonitrile (II). The compounds are thusly prepared by reacting α-phenyl-α-(2-pyridyl) acetonitrile with a selected 1-R-3-halopyrrolidine (III) or a 1-R-3-pyrrolidinyl-α-phenyl-α-(2-pyridyl)acetonitrile. The thusly prepared acetonitriles are within the scope of Formula I and also serve as intermediates for the preparation of the 1-R-3-pyrrolidinyl-α-phenyl-α-(2-pyridyl)acetamides and the 1-R-3-pyrrolidinyl-α-phenyl-α-(2-pyridyl)methanes of Formula I. The foregoing reactions are in accord with the following graphic reaction sequence:

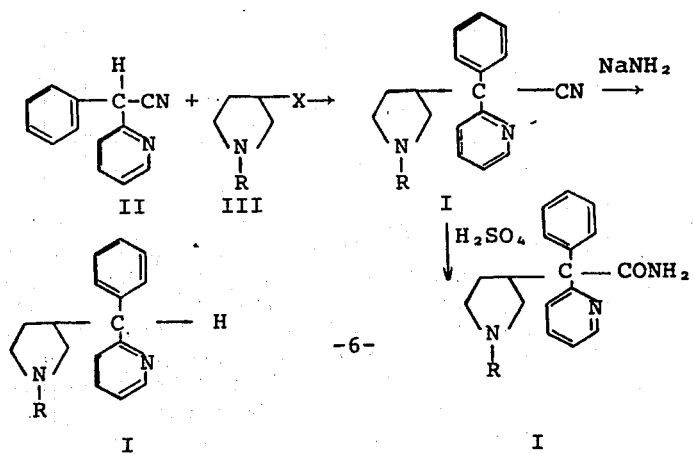

wherein R has the value assigned hereinabove, Y of general Formula I is shown as —CN, —CONH, and —H and X is a halide, preferably chlorine, or a tosylate group.

The 1-R-3-pyrrolidinyl-α-phenyl-α-phenyl-α-(2-pyridyl)acetonitriles are generally prepared by alkylating the alkali metal, e.g., sodium, salt of α-phenyl-α-(2-pyridyl)acetonitrile with the appropriate 1-R-3-halo (e.g., chloro) pyrrolidine or the appropriate 1-R-3-pyrrolidinyltosylate in a suitable solvent such as dry toluene. The sodium salt of α-phenyl-α-(2-pyridyl) acetonitrile is formed by reaction of the nitrile with an alkali metal amide, e.g., sodamide, in a dry solvent, e.g., toluene. The condensation with the 3-chloropyrrolidine or the 3-pyrrolidinyltosylate is usually carried out with the application of heat, e.g., in refluxing benzene, toluene, or like solvent for an extended period, e.g., approximately 3 hours. The solvent, e.g., toluene solution, is then washed with water and the product extracted as with one normal hydrochloric acid. The acid extract may then be basified with sodium hydroxide, extracted with a water-insoluble solvent such as ether or chloroform, the solution washed and dried, as over sodium sulfate, concentrated, and the residue distilled in vacuo.

The 1-R-3-pyrrolidinyl-α-phenyl-α-(2-pyridyl)acetonitriles are heated in concentrated sulfuric acid for a period of from about 15 hours to about 30 hours at a temperature of from about 50° to about 80°C., preferably at 60° to 70°C. The acidic mixture is cooled and maintained below about 50°C. while the solution is basified using a strongly basic solution as, for example, 50% sodium hydroxide; the acetamide products are extracted with a suitable solvent such as chloroform or ethyl acetate, the extract concentrated and the products allowed to separate from the concentrated solutions.

The 1-R-3-pyrrolidinyl-α-phenyl-α-(2-pyridyl)methanes of Formul I are prepared by refluxing a mixture of the precursor acetonitriles and sodium amide in a dry aprotic solvent as, for example, toluene, for a period of from about 20 hours to about 30 hours. The cooled mixtures are diluted with water, the organic layers separated, dried over a suitable drying agent such as sodium sulfate, the dried solutions filtered and concentrated and the residual products isolated by a suitable procedure such as vacuum distillation or conversion to an acid addition salt which is further purified by crystallization.

PREPARATION 1

αPhenyl-α-(2-pyridyl)acetonitrile

Phenylacetonitrile 46.8 grams (0.40 mole) was added dropwise to a stirred suspension of 31.2 g. (0.80 mole) of powdered sodium amide in 200 ml. of dry toluene in an oven-dried, 2-liter, three-neck round bottom flask, equipped with dropping funnel, thermometer, stirrer and sodium hydroxide-protected condenser. During the addition, the temperature was maintained at 30°–35°C. with ice bath cooling. Afterwards, the mixture was brought slowly to reflux and maintained there for 4½ hours with continuous stirring. Then 63.6 grams (0.40 mole) of 2-bromopyridine in 100 ml. of toluene was added dropwise at a rate which maintained refluxing of the solution. After complete addition, stirring and refluxing was continued for 3 hours. The mixture was then cooled at 25°C. and ca. 300 ml. of water was added, at first very cautiously and then in a steady stream. The phases were separated and the toluene layer extracted with ca. 150 ml. of water, and then with several portions of cold 6 N hydrochloric acid. The acid extracts were basified with 50% sodium hydroxide with cooling and extracted with ether. The ether extract was washed with water, dried over sodium sulfate and concentrated, and the residue was distilled. Yield, 41.7 g. (54 %); b.p. 134°–136°C./0.07 mm. The distillate crystallized and after recrystallization from isopropyl ether melted at 87°–88.5°C.

Analysis: Calculated for $C_{13}H_{10}N_2$: C,80.39; H,5.19; N,14.42. Found: C,80.42; H,5.35; N,14.14.

EXAMPLE 1

1-n-Butyl-3-pyrrolidinyl-α-phenyl-α-(2-pyridyl)acetonitrile

A solution of 58.5 grams (0.30 mole) of α-phenyl-α-(2-pyridyl)acetonitrile in 200 ml. of dry toluene was added dropwise to a stirred suspension of 12.8 grams (0.33 mole) of sodium amide in 300 ml. of dry toluene contained in a 2 liter, three-neck, round-bottom flask, equipped with dropping funnel, mechanical stirrer, thermometer and sodium hydroxide-protected condenser. During the addition, the mixture was maintained below 35°C. by ice bath cooling. It was then brought to reflux and maintained there with continued stirring for 4½ hours, after which 48.5 grams (0.30mole) of 1-n-butyl-3-chloropyrrolidine was added dropwise with stirring and refluxing continued for another 3 hours. The mixture was then cooled to 25°C. and 200 ml. of water was added, at first cautiously and then in a stream. The phases were separated and the toluene layer was extracted with about 200 ml. of water and then with several portions of 6 N hydrochloric acid. The acid extracts were basified with 50% sodium hydroxide with cooling and extracted with several portions of ether. The ether extracts were washed with water, dried over sodium sulfate, concentrated and the residue was distilled. Yield, 56.6 grams (59%); b.p. 170°–175°C./0.08 mm.

Analysis: Calculated for $C_{21}H_{25}N_3$: C,78.96; H,7.89. Found: C,78.87; H,8.06.

EXAMPLE 2

1-Methyl-3-pyrrolidinyl-α-phenyl-α-(2-pyridyl)acetonitrile

Utilizing the procedure of Example 1, 58.5 grams (0.30 mole) of α-phenyl-α-(2-pyridyl)acetonitrile in 100 ml of dry toluene was alkylated using 35.8 grams (0.30 mole) of 1-methyl-3-chloropyrrolidine and 12.8 grams (0.33 mole) of sodium amide. There was obtained 19.5 grams (23%) of the title product which was collected at 148°–151°C./0.07 mm.

Analysis: Calculated for $C_{18}H_{20}N_2$: C,77.94 H,6.91. Found: C,78.21 H,7.05.

EXAMPLE 3

1-Isopropyl-3-pyrrolidinyl-α-phenyl-α-(2-pyridyl)acetonitrile

Utilizing the procedure of Example 1, 58.5 grams (0.30 mole) of α-phenyl-α-(2-pyridyl)acetonitrile was alkylated in 100 ml. of dry toluene using 40.0 grams (0.30 mole) of 1-isopropyl-3-chloropyrrolidine and 12.8 grams (0.33 mole) of sodium amide. The reaction mixture was worked up to give 39 grams (43%) of product which distilled at 154°–156°C./0.03 mm. The distilled oil was crystallized from isopropyl ether and the crystalline product melted at 107°–109°C.

Analysis: Calculated for $C_{20}H_{23}N_3$: C,78.65; H,7.59. Found: C,78.88; H,7.81.

EXAMPLE 4

1-Cyclohexyl-3-pyrrolidinyl-α-phenyl-α-(2-pyridyl)acetonitrile

Utilizing the procedure of Example 1, there was obtained from 58.5 grams (0.30 mole) of α-phenyl-α-(2-pyridyl)acetonitrile, 56.3 grams (0.30 mole) of 1-cyclohexyl-3-chloropyrrolidine and 12.8 grams (0.33 mole) of sodium amide, 53.9 grams (52%) of the title product at 200°–208°C./0.05 mm.

Analysis: Calculated for $C_{23}H_{27}N_3$: C,79.96; H,7.88. Found: C,80.15; H,8.06.

EXAMPLE 5

1-Isobutyl-3-pyrrolidinyl-α-phenyl-α-(2-pyridyl)acetonitrile

Using the procedure of Example 1, there was obtained by reacting 58.5 g. (0.30 mole) of α-phenyl-α-(2-pyridyl)acetonitrile, 48.5 g. (0.30 mole) of 1-isobutyl-3-chloropyrrolidine and 12.8 g. (0.33 mole) of sodium amide in dry toluene, 58.7 g. (61%) of the title product which distilled at 154°–157°C./0.09 mm.

Analysis: Calculated for $C_{21}H_{20}N_3$: C,78.96; H,7.89. Found: C,79.28; H,8.14.

EXAMPLE 6

1-Benzyl-3-pyrrolidinyl-α-phenyl-α-(2-pyridyl)acetonitrile

Utilizing the procedure of Example 1, 58.5 g. (0.30 mole) of α-phenyl-α-(2-pyridyl)acetonitrile was alkylated in dry toluene using 58.5 g. (0.30 mole) of 1-benzyl-3-chloropyrrolidine and 12.8 g. (0.33 mole) of sodium amide. There was obtained 52.0 g. (49%) of product at 200°–210°C./0.08 mm.

Analysis: Calculated for $C_{24}H_{23}N_3$: C,81.55; H,6.56. Found: C,81.69; N,6.77.

EXAMPLE 7

1-Ethyl-3-pyrrolidinyl-α-phenyl-α-(2-pyridyl)acetamide

1-Ethyl-3-pyrrolidinyl-α-phenyl-α-(2-pyridyl)acetonitrile (10.0 g.; 0.029 mole) and 40 ml. of concentrated sulfuric acid was stirred for 24 hours at 60°–70°C. The cooled reaction mixture was basified using 50% sodium hydroxide, keeping the temperature below 50°C. during the basification. The basic mixture was extracted with ethyl acetate, the combined extracts were filtered and concentrated to a small volume and set aside to cool. The white crystalline product which separated from the cooled solution was collected by filtration and washed with ethyl acetate. The crude product which melted at 151.5°–156°C. was recrystallized three times from ethyl acetate to give material which melted at 161°–162°C.

Analysis: Calculated for $C_{19}H_{23}N_{30}$: C,73.75; H,7.49; N,13.58. Found: C,73.78; H,7.58; N,13.69.

EXAMPLE 8

1-Methyl-3-pyrrolidinyl-α-phenyl-α-(2-pyridyl)acetamide

Sixty-two and six-tenths g.(0.244 mole) of 1-methyl-3-pyrrolidinyl-α-phenyl-α-(2-pyridyl)acetonitrile and 240 ml. of concentrated sulfuric acid was stirred at 70°C. for 24 hours. The reaction mixture was poured onto ice, the cold solution was basified using 50% sodium hydroxide and the base insoluble oil was extracted using ethyl acetate. The ethyl acetate extract was dried, filtered and concentrated to a small volume. The solid which separated from the cold concentrated solution weighed 42 g. and melted at 148°–150°C. The material was recrystallized from ethyl acetate and ethanol several times to a constant melting point of 150°–153°C.

Analysis: Calculated for $C_{18}H_{21}N_{3O}$: C,73.19; H,7.17; N,14.23. Found: C,73.40; H,7.23; N,14.28.

EXAMPLE 9

1-Isopropyl-3-pyrrolidinyl-α-phenyl-α-(2-pyridyl)acetamide

Utilizing the procedure of Example 8, 36.47 g. (0.12 mole) of 1-isopropyl-3-pyrrolidinyl-α-phenyl-α-(2pyridyl)acetonitrile and 160 ml. of concentrated sulfuric acid were mixed and heated at 70°C. and worked up to give 25 g. of white crystalline product which melted at 130°–134°C. The material was recrystallized from ethyl acetate to a constant melting point of 127.5°–133°C.

Analysis: Calculated for $C_{20}H_{25}N_{3O}$: C,73.81; H,7.47; N,12.91. Found: C,73.95; H,7.65; N,12.67.

EXAMPLE 10

1-n-Butyl-3-pyrrolidinyl-α-phenyl-α-(2-pyridyl)acetamide

The title compound was prepared by acid hydrolysis of 1-n-butyl-3-pyrrolidinyl-α-phenyl-α-(2-pyridyl)acetonitrile using concentrated sulfuric acid, and the procedure of Example 7. The product was repeatedly recrystallized from ethyl acetate to a constant melting point of 108°–111°C.

Analysis: Calculated for $C_{21}H_{27}N_{3O}$: C,74.74; H,8.07; N,12.45. Found: C,74.97; H,8.21; N,12.46.

EXAMPLE 11

1-n-Butyl-3-pyrrolidinyl-α-phenyl-α-(2-pyridyl)methane

A solution of 63.8 g. (0.20 mole) of 1-n-butyl-3-pyrrolidinyl-α-phenyl-α-(2-pyridyl)acetonitrile in approximately 200 ml. of dry toluene was added at a rapid drop to a suspension of 19.5 g. (0.5 mole) of sodium amide in 300 ml. of dry toluene contained in a 2 liter, three-neck round bottom flask equipped with dropping funnel, mechanical stirrer and condenser with sodium hydroxide drying tube. The mixture was refluxed and stirred for approximately 25 hours, cooled to 20°C. and 150 ml. of water was added, at first cautiously and then in a steady stream. The mixture was then transferred to a 2 liter separatory funnel, the aqueous layer separated and discarded. The organic portion was washed once more with approximately 150 ml. of water, dried over sodium sulfate, concentrated and the residue distilled. Yield, 24.9 g. (42%); b.p. 175°–183°/0.04 mm.

Analysis: Calculated for $C_{20}H_{26}N_2$: C,81.58; H,8.90; N,9.52. Found: C,81.40; H,8.99; N,9.37.

EXAMPLE 12

1-Isobutyl-3-pyrrolidinyl-α-phenyl-α-(2-pyridyl)methane

Utilizing the procedure of Example 11, 63.8 g. (0.20 mole) of 1-isobutyl-3-pyrrolidinyl-α-phenyl-α-(2-pyridyl)acetonitrile was converted to the title compound. The product was isolated and distilled at 142°–144°C./0.006 mm. to give 23 g. of product.

Analysis: Calculated for $C_{20}H_{26}N_2$: C,81.58; H,8.90; N,9.52. Found: C,81.48; H,9.18; N,9.50.

EXAMPLE 13

1-Benzyl-3-pyrrolidinyl-α-phenyl-α-(2-pyridyl)methane

Utilizing the procedure of Example 11, 1-benzyl-3-pyrrolidinyl-α-phenyl-α-(2-pyridyl)acetonitrile was converted to the title compound. The material was collected at 180°–190°C./0.04 mm. to give 46% yield product.

Analysis: Calculated for $C_{23}H_{24}N_2$: C,84.10; H,7.37; N,8.53. Found: C,84.38; H,7.58; N,8.79.

EXAMPLE 14

1-Isopropyl-3-pyrrolidinyl-α-phenyl-α-(2-pyridyl)methane maleate

Utilizing the procedure of Example 11, 61.2 g. (0.20 mole) of 1-isopropyl-3-pyrrolidinyl-α-phenyl-α-(2-pyridyl)acetonitrile was converted to 1-isopropyl-3-pyrrolidinyl-α-phenyl-α-(2-pyridyl)methane. The maleate salt was prepared by dissolving 39.2 g. of the free base in 125 ml. of ethyl acetate, adding 16.15 g. of maleic acid to the mixture and heating the mixture to effect solution. Solution was allowed to cool and the maleate salt was collected to give maleate salt melting at 108°–110.5°C.

Analysis: Calculated for $C_{23}H_{28}N_2O_4$: C,69.67; H,7.12; N,7.07. Found: C,69.42; H,7.33; N,6.87.

The invention further provides pharmaceutical compositions comprising as active ingredient, at least one of the compounds according to the invention in association with a pharmaceutical carrier or excipient. The compounds may be presented in a form suitable for oral, parenteral or intracardial administration, or in a form suitable for inhalation. Thus, for example, compositions for oral administration are solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed antiarrhythmic effective dose of active ingredient. Tablets, coated tablets, capsules, and ampoules are examples of preferred dosage unit forms according to the invention. Each dosage unit adapted for oral administration may conveniently contain 5 to 100 mg., and preferably 25 to 75 mg., of the active ingredient; each dosage unit adapted for intracardial, intravenous, or inhalation administration may conveniently contain 1 to 20 mg, and preferably 5 to 10 mg of the active ingredient; whereas each dosage unit adapted for intramuscular administration may conveniently contain 10 to 100 mg and preferably 20 to 80 mg of the active ingredient.

Examples of compositions within the preferred ranges given are as follows:

| CAPSULES | |
|---|---|
| Ingredients: | Per cap., mg |
| 1. Active ingredient | 5.0 |
| 2. Lactose | 140.0 |
| 3. Magnesium stearate | 4.0 |

Procedure:
(1) Blend 1, 2 and 3.
(2) Mill this blend and blend again.
(3) This milled blend is then filled into No. 1 hard gelatin capsules.

| TABLETS | |
|---|---|
| Ingredients: | Mg/tabl,mg |
| 1. Active ingredient | 5.0 |
| 2. Corn starch | 20.0 |
| 3. Kelacid | 20.0 |
| 4. Keltose | 20.0 |
| 5. Magnesium stearate | 1.5 |

Procedure:
1. Blend 1, 2, 3 and 4.
2. Add sufficient water portionwise to the blend from step No. 1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140°F.
5. The dried granules are then passed through an oscillating granulator, using a 10-mesh screen.
6. Lubricate the dry granules with 0.5% magnesium stearate.
7. The lubricated granules are compressed on a suitable tablet press.

| INTRAVENOUS INJECTION | |
|---|---|
| Ingredients: | |
| 1. Active ingredient | mg. 5.0 |
| 2. pH 4.0 buffer solution, q.s. to | ml. 1.0 |

Procedure:
1. Dissolve the active ingredient in the buffer solution.
2. Aseptically filter the solution from Step No. 1.
3. The sterile solution is now aseptically filled into sterile ampoules.
4. The ampoules are sealed under aseptic conditions.

| INTRAMUSCULAR INJECTION | |
|---|---|
| Ingredients: | |
| 1. Active ingredient | mg. 5.0 |
| 2. Isotonic buffer solution 4.0, q.s. to | ml. 2.0 |

Procedure:
1. Dissolve the active ingredient in the buffer solution.
2. Aseptically filter the solution from Step No. 1.
3. The sterile solution is now aseptically filled into sterile ampoules.
4. The ampoules are sealed under aseptic conditions.

| INHALATION | |
|---|---|
| Ingredients: | |
| 1. Active ingredient | mg. 100 |
| 2. Alcohol 95%, q.s. | cc. 1.0 |

Procedure:
1. Dissolve No. 1 and No. 2.
2. This solution is properly packaged in an aerosol dispenser containing a metered valve and suitable propellant.

What is claimed is:
1. A composition for controlling cardiac arrhythmias with minimal side effects, comprising (1) an antiarrhythmic effective amount of between about 1 and 100 mg. of a compound of the formula:

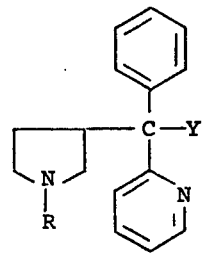

wherein;
R is a member selected from the group consisting of loweralkyl, lower cycloalkyl or phenyl loweralkyl;
Y is a member selected from carbamoyl, cyano or hydrogen, and (2) a pharmaceutical carrier.
2. The composition of claim 1 wherein R is loweralkyl.
3. The composition of claim 2 wherein the compound is 1-isopropyl-3-pyrrolidinyl-α-phenyl-α-(2-pyridyl)acetonitrile.
4. The composition of claim 2 wherein the compound is 1-methyl-3-pyrrolidinyl-α-phenyl-α-(2-pyridyl)acetamide.
5. The composition of claim 2 wherein the compound is 1-isopropyl-3-pyrrolidinyl-α-phenyl-α-(2-pyridyl)acetamide.
6. The composition of claim 2 wherein the compound is 1-n-butyl-3-pyrrolidinyl-α-phenyl-α-(2-pyridyl)acetamide. g,21
7. The composition of claim 1 wherein the compound is -benzyl-3-pyrrolidinyl-α-phenyl-α-(2-pyridyl)acetonitrile. administering
8. A method of controlling cardiac arrhythmias in a living animal body which comprises ad ministering to said living animal body an antiarrhythmic effective amount of a compound of the formula:

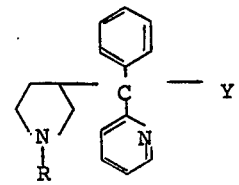

wherein;

R is a member selected from the group consisting of loweralkyl, lowercycloalkyl or phenyl lower alkyl, Y is a member selected from the group consisting of carbamoyl, cyano or hydrogen, and pharmaceutically acceptable acid addition salts thereof.

9. The method of claim 8 wherein R is loweralkyl.

10. The method of claim 9 wherein the compound is 1-isopropyl-3-pyrrolidinyl-α-phenyl-α-(2-pyridyl)acetonitrile.

11. The method of claim 9 wherein the compound is 1-methyl-3-pyrrolidinyl-α-phenyl-α-(2-pyridyl)acetamide.

12. The method of claim 9 wherein the compound is 1-isopropyl-3-pyrrolidinyl-α-phenyl-α-(2-pyridyl)acetamide.

13. The method of claim 9 wherein the compound is 1-n-butyl-3-pyrrolidinyl-α-phenyl-α-(2-pyridyl)acetamide.

14. The method of claim 8 wherein the compound is 1-benzyl-3-pyrrolidinyl-α-phenyl-α-(2-pyridyl)acetonitrile.

* * * * *